(12) United States Patent
Gupta

(10) Patent No.: US 7,597,879 B2
(45) Date of Patent: Oct. 6, 2009

(54) SUNSCREEN SAFETY AND EFFICACY ENHANCEMENT

(75) Inventor: Shyam K Gupta, Scottsdale, AZ (US)

(73) Assignee: Bioderm Research, Scottsdale, AZ (US)

( * ) Notice: Subject to any disclaimer, the term of this patent is extended or adjusted under 35 U.S.C. 154(b) by 0 days.

(21) Appl. No.: 11/676,284

(22) Filed: Feb. 17, 2007

(65) Prior Publication Data

US 2007/0189992 A1 Aug. 16, 2007

Related U.S. Application Data

(63) Continuation-in-part of application No. 11/308,290, filed on Mar. 15, 2006, which is a continuation-in-part of application No. 10/306,948, filed on Nov. 29, 2002, now abandoned, and a continuation-in-part of application No. 10/710,011, filed on Jun. 11, 2004, now abandoned.

(51) Int. Cl.
*A61K 8/00* (2006.01)
*A61K 8/18* (2006.01)
*A61Q 17/04* (2006.01)
*C07D 231/00* (2006.01)

(52) U.S. Cl. .......................... 424/59; 548/104; 424/401
(58) Field of Classification Search ................. 548/104; 424/59, 401
See application file for complete search history.

(56) References Cited

U.S. PATENT DOCUMENTS

2006/0110415 A1* 5/2006 Gupta .................... 424/401
2006/0127430 A1* 6/2006 Gupta .................... 424/401

* cited by examiner

*Primary Examiner*—Johann R Richter
*Assistant Examiner*—Luke E Karpinski

(57) ABSTRACT

The present invention discloses safety and efficacy enhancement of sunscreens with certain heterocyclic base complexes of manganese via urocanate pathway modulation. The present invention also discloses a method for topical application of said complexes, which causes the reduction of topical peroxide including hydrogen peroxide, the reduction of topical inflammation including sunburn, increased sun protection of skin, the reduction of skin wrinkles, comprehensive protection from UVA, UVB, and UVC, and reduction of radiation-initiated inflammation.

20 Claims, No Drawings

SUNSCREEN SAFETY AND EFFICACY ENHANCEMENT

The present invention is a continuation-in-part of U.S. patent application Ser. No. 11/308,290; filed Mar. 15, 2006, which is a continuation-in-part of U.S. patent application Ser. No. 10/306,948 filed Nov. 29, 2002, now abandoned. The present invention is also a continuation-in-part of U.S. patent application Ser. No. 10/710,011, filed Jun. 11, 2004 now abandoned.

BACKGROUND OF THE INVENTION

The present invention discloses safety and efficacy enhancement of sunscreens with certain heterocyclic base complexes of manganese via urocanate pathway modulation. The present invention also discloses a method for topical application of said complexes, which causes the reduction of topical peroxide including hydrogen peroxide, the reduction of topical inflammation including sunburn, increased sun protection of skin, the reduction of skin wrinkles, comprehensive protection from UVA, UVB, and UVC, and reduction of radiation-initiated inflammation.

DETAILED DESCRIPTION

The present invention discloses safety and efficacy enhancement of sunscreens with certain heterocyclic base complexes of manganese via urocanate pathway modulation. The topical application of compositions of the present invention causes the reduction of topical peroxide including hydrogen peroxide, the reduction of topical inflammation including sunburn, increased sun protection of skin, the reduction of skin wrinkles, comprehensive protection from UVA, UVB, and UVC, and reduction of radiation-initiated inflammation.

The present invention also relates to a method for topical application of certain heterocyclic complexes of manganese as catalase mimetics for the reduction of topical hydrogen peroxide, the latter known to be formed by the action of UV on certain sunscreen agents in the presence of moisture. This results in the enhancement of both the safety and efficacy of said sunscreen agents. The method of topical delivery of the present invention comprises; (i) mixing of a manganese complex of a nitrogen heterocyclic base, wherein manganese is covalently bound to at least two oxygen atoms and, wherein, said base having at least one nitrogen atom in its ring structure coordinately bound to said manganese, and having general chemical structure according to [FIG. 1]; and (ii) a sunscreen agent; and (iii) topical application of said mixture. Alternatively, said manganese complex can be generated on-site on skin surface by the reaction of a manganese donor agent with a suitable nitrogen heterocyclic base already present on skin surface. A cosmetically or pharmaceutically acceptable carrier base can also be included with the said mixture.

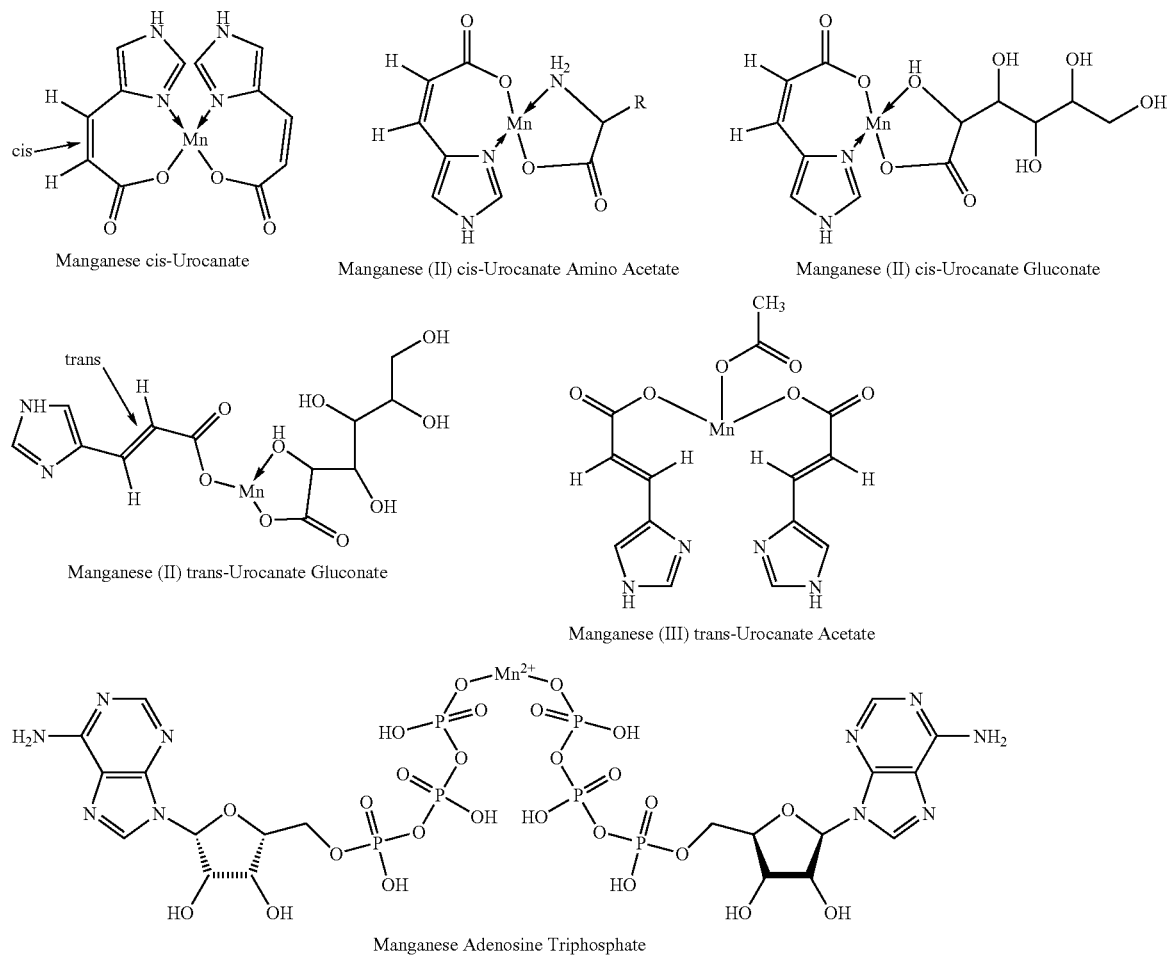

Manganese cis-Urocanate

Manganese (II) cis-Urocanate Amino Acetate

Manganese (II) cis-Urocanate Gluconate

Manganese (II) trans-Urocanate Gluconate

Manganese (III) trans-Urocanate Acetate

Manganese Adenosine Triphosphate

-continued

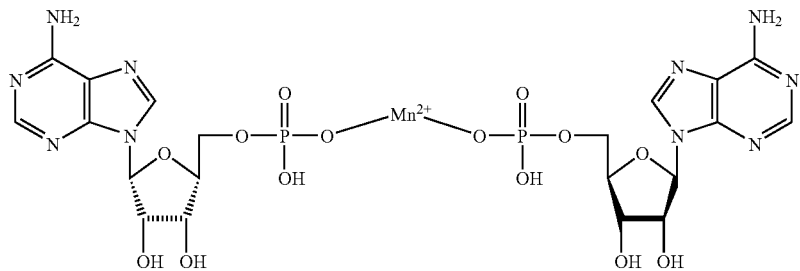
Manganes Adenosine Phosphate

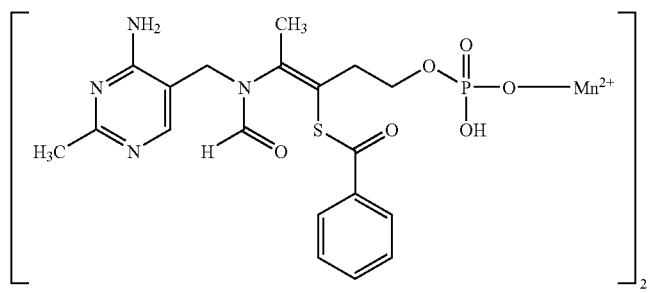
Manganese Benfotiamine

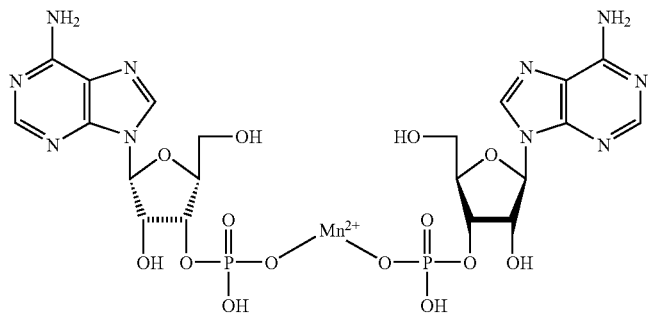
Manganese Adenosine Phosphate (chain state)

The said method causes the reduction of peroxides, such as hydrogen peroxide, formed from the exposure of a sunscreen agent to UV or solar radiation in the presence of topical moisture on skin. The said method is useful for enhancing the safety and efficacy of topical sunscreen agents. The anti-inflammatory, wrinkles reduction, skin aging control, cellular antioxidant, and skin damage control benefits that are a result of the reduction of said peroxides on skin are also provided by the method of the present invention.

Sunscreen compositions, which protect skin from the damaging effects of solar UV, are now widely used by consumer for their various protective benefits, for example, skin cancer, collagen breakdown, abnormal elastin accumulation, free radicals accumulation that damages cell function and alters genetic material, and certain chemicals that are released that suppresses the immune system.

Sunscreens offer full protection against UVB, but not UVA. Very few sunscreen ingredients protect against UVA. Three types of UV is given off by the sun; (1) UVC (100-290 nm): it is absorbed by the ozone and doesn't affect the skin, as it usually does not reach the Earth; (2) UVB (290-320 nm): it affects the outer layer of the skin and is the primary cause of sunburn. It is most intense between 10-2 and during the summer months; and (3) UVA (320-400 nm): it penetrates deeper into the skin and the intensity is more constant than UVB without variations through the day and year. These aspects have been further discussed in detail elsewhere, for example, Reisch et al. [Chemical & Engineering News, 83, 18 (2005].

It is now becoming clear that certain sunscreens cause the formation of hydrogen peroxide upon their exposure to UV in the presence of moisture. It is actually this peroxide that causes the breakdown of collagen, damages to cell function, and suppression of the immune system.

It is also becoming clear that urocanic acid, formed from the action of Histidine Ammonia Lyase on L-Histidine, which acts as a natural sunscreen agent on skin, for example Stab et al., U.S. Pat. No. 5,620,680, is converted into its cis-isomer upon exposure to UV, the latter then catalyzes the formation of various peroxide species via a cascade of urocanate pathway biochemical steps [FIG. 2]:

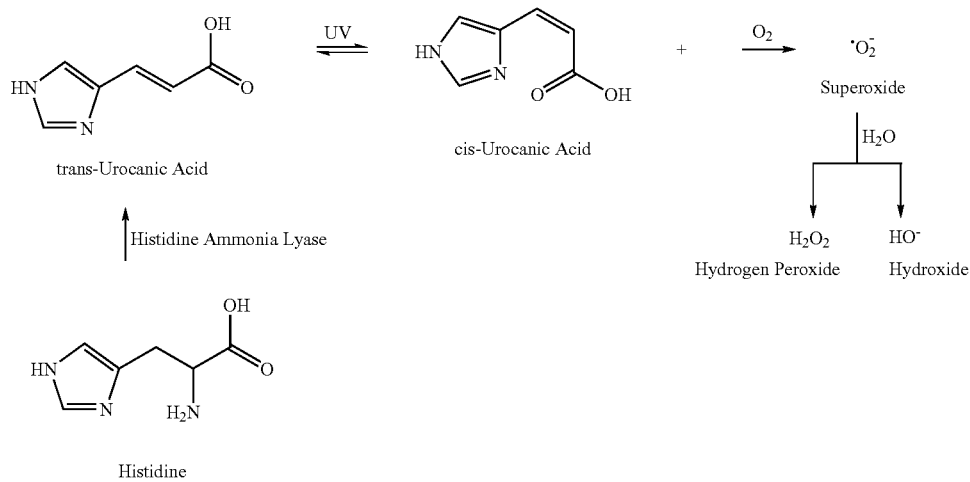

Fig. 2. Urocanate Pathway for Peroxide Formation

The role of manganese in enhancing the efficacy of sunblock agents has been recognized very recently. For example, manganese ions introduce extra energy levels in titanium dioxide, a very popular sun-block agent. These energy levels sit in the UVA portion of the absorption band. This allows for the higher absorption levels for titanium dioxide. Manganese also causes the free radical scavenging on skin [FIG. 3]:

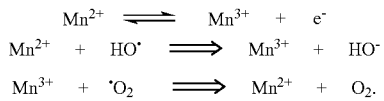

Fig. 3. Free Radical Scavenging by Manganese Ions $Mn^{2+}$ ⇌ $Mn^{3+}$ + $e^-$
$Mn^{2+}$ + $HO^{\cdot}$ ⟹ $Mn^{3+}$ + $HO^-$
$Mn^{3+}$ + $^{\cdot}O_2$ ⟹ $Mn^{2+}$ + $O_2$.

Manganese doping of sun-block agents has thus become a recent practice. Wakefield et al. [Photochem. Photobiol. Sci., 3, 648 (2004)] report the effect of manganese doping on the free radical generation rate, free radical scavenging, and UVA absorption properties of titania. These authors do not disclose any peroxide reducing benefits of said doping. Wakefield et al. do not disclose any methods for the said doping of any organic sunscreen agents.

In a product description, Oxonica (www.oxonica.com) similarly discloses manganese doping of titanium dioxide for free radical scavenging benefits. Any methods for the said doping of any organic sunscreen agents and its effect on peroxide degradation were not disclosed.

Sakurai et al. [Photochem. Photobiol Sci., 4, 715 (2005] disclose the harmful effects of ultraviolet (UV) exposure on the skin that are associated with the generation of reactive oxygen species (ROS) such as superoxide anion radical [O(2)(-)], hydrogen peroxide [H(2)O(2)], hydroxyl radical (OH), and singlet oxygen [(1)O(2)] as well as lipid peroxides and their radicals (LOOH and LOO). Again, the problem was identified, but no solutions were proposed.

Hayashi et al. [Toxicol. Lett., 167, 1 (2006)] disclose benzophenone (BP) to be a suspected endocrine disrupter that is found in the environment. BP undergoes metabolic and photochemical activation. Hayashi et al. identified photoproducts of BP using high-performance liquid chromatography and mass spectrometry, and determined their estrogenic activity using both in vitro and in vivo assays. Although BP showed no estrogenic activity, two estrogenic photoproducts were detected after irradiating an aqueous solution of BP with UV or sunlight. These active products were identified as 3-hydroxy BP (BP-3OH) and 4-hydroxyBP (BP-4OH). The formation of hydrogen peroxide H2O2) was detected with increasing levels of UV, and the addition of H2O2 to the BP solution increased BP-3OH and BP-4OH production under UV irradiation. BP hydroxylation was also observed in the reaction with the Fenton reagent generating hydroxyl radical without UV irradiation. These results suggest the involvement of photochemically generated H2O2 and hydroxyl radical in the BP hydroxylation. BP-4OH was more potent than BP-3OH for promoting estrogen receptor (ER)-mediated transcription and uterotrophic activity, although both of them showed same affinity in ER binding. In conclusion, BP can be converted into ring-hydroxylated derivatives that have estrogenic activity after exposure to light. While Hayashi et al. did show harmful effects of a commonly used sunscreen agent, such as benzophenine-3, including peroxide formation, they did not disclose any solution to this problem.

Yashui et al., [Biochem. Biophys. Res. Commun., 269, 131 (2000)] report that the recent increase of ultraviolet (UV) rays on Earth due to the increasing size of the ozone hole is suggested to be harmful to life and to accelerate premature photoaging of the skin. The detrimental effects of UV radiation on the skin are associated with the generation of reactive oxygen species (ROS) such as superoxide anion radical, hydrogen peroxide (H(2)O(2)), hydroxyl radical (HO.), and singlet oxygen [(1)O(2)]. However, direct proof of such ROS produced in the skin under UV irradiation has been elusive. In this study, Yashui et al. report first in vivo detection and imaging of the generated ROS in the skin of live mice following UVA irradiation, in which both a sensitive and specific chemiluminescence probe (CLA) and an ultra low-light-imaging apparatus with a CCD camera were used. In addition, these authors found that superoxide radical anion is formed spontaneously and (1)O(2) is generated in the UVA-irradiated skin.

Nishimura et al: [Exp. Dermatol., 15, 891 (2006)] have shown the formation of reactive oxygen species (ROS) in the skin induced by the ultraviolet (UV) light that has been shown to lead to many cutaneous disorders, skin cancer and photo ageing, the mechanism and distribution of ROS generation has not yet been definitively determined. Nishimura et al. have thus shown that ROS induced by UVA exposure occurs and distributes in the outermost layer of the stratum corneum.

Radschuweit et al. [Photobiol. Photobiol., 73, 119 (2001] report topical application of Ketoprofen (KP), which is a potent nonsteroidal anti-inflammatory drug, to be problematic because the photosensitizing properties of the benzophenone moiety that may cause phototoxic effects when the treated skin region is exposed to UVA light. Using capillary electrophoresis with electrochemical detection a high amount of hydrogen peroxide was found among the reaction products. This shows potential for harmful effects on topical application of other benzophenone derivatives, such as certain organic sunscreen agents.

Patt (U.S. patent application Ser. No. 20060246029) discloses certain peptide manganese complexes, which also contain retinal, for the treatment of photo-damaged skin. Patt does not disclose any peroxide reducing benefits of said manganese complexes.

Patt (U.S. patent application Ser. No. 20060018851) also discloses the treatment for hyperpigmentation with certain peptide manganese complexes, which also contain retinal. Patt does not disclose any peroxide reducing benefits of said manganese complexes.

Manganese complexes have been known for some time, for example, Gupta (U.S. patent application Ser. No. 20060183708), which does not disclose any peroxide reducing benefits of said complexes on their topical application. San et al. [Z. Naturforsch., 59, 692 (2004)] disclose certain metal complexes of amino acid Schiff's bases.

Sayre et al. [Photochem. Photobiol., 81, 452 (2005)] report the formation of free-radicals upon exposure of organic sunscreens to UV. While it did show the problem, Sayre et al. did not produce a solution.

From the above discussion it is clear that hydrogen peroxide and other peroxy species are formed on skin surface by the action of UV. The formation of such peroxides increases in the presence of certain sunscreen and sun-block agents. The harmful effects of such accumulation of peroxide species on skin are also well recognized by the medical and scientific community. It is thus surprising that no effective solution to this problem has been disclosed until the present invention.

In an unexpected and surprising discovery, the present invention discloses certain manganese complexes of nitrogen heterocyclic bases, wherein manganese is covalently bound to at least two oxygen atoms and coordinately bound to at least one nitrogen atom, and having general chemical features shown in [FIG. 1], that cause a reduction of peroxide species on skin. This benefit is provided even when said manganese complexes of nitrogen heterocyclic bases are used in combination with a sunscreen or sun-block agent(s). A method for the topical application of said manganese complexes of nitrogen heterocyclic bases to provide said reduction of peroxide species on skin is also disclosed. A covalent bond is formed by the sharing of electrons between two atoms. A coordinate bond, or dative bond, is formed when an electron-donor species (a Lewis-base) donates a pair of electrons to an electron acceptor species (a Lewis-acid).

Urocanic acid, as discussed above, catalyzes the formation of peroxides from the action of UV on skin. In a yet another surprising discovery, certain manganese derivatives of urocanic acid, have now been found to catalyze the decomposition of said peroxides on skin. It is postulated that said manganese derivative of urocanic acid first undergoes a photoisomerization, and the photoisomerized form subsequently causes the decomposition of peroxides [FIG. 4]:

Fig. 4. Manganese Urocanate Photoisomerism

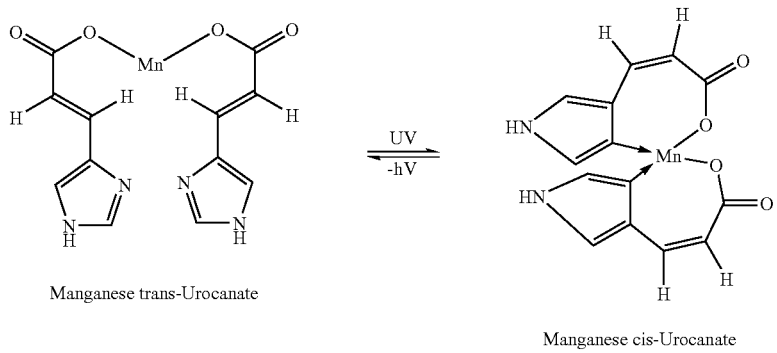

Manganese trans-Urocanate

Manganese cis-Urocanate

The manganese complexes of the present invention can also be in an open configuration, such as manganese complexes of certain nucleotide bases, as exemplified in [FIG. 5].

Fig. 5. Manganese Complexes of Nucleotide Bases

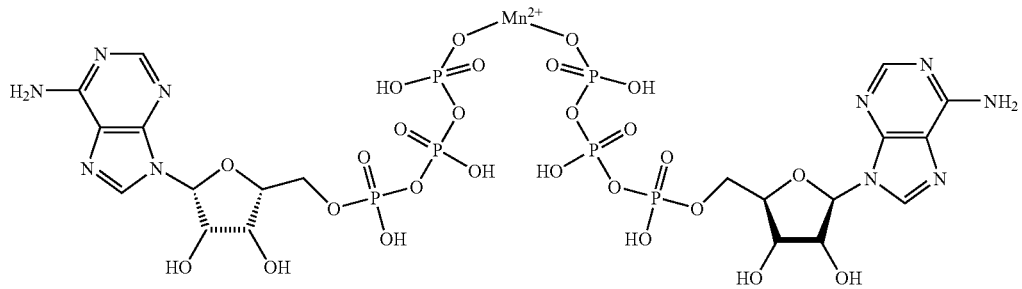

Manganese Adenosine Triphosphate

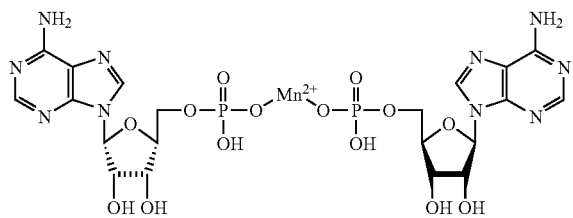

Manganese Adenosine Phosphate

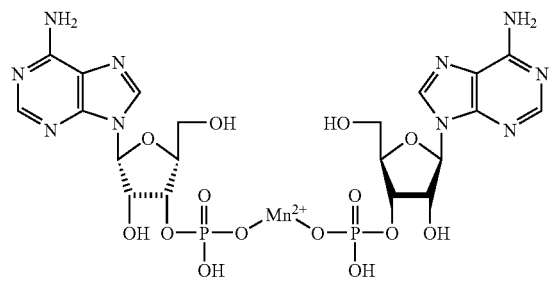

Manganese Adenosine Phosphate (chain state)

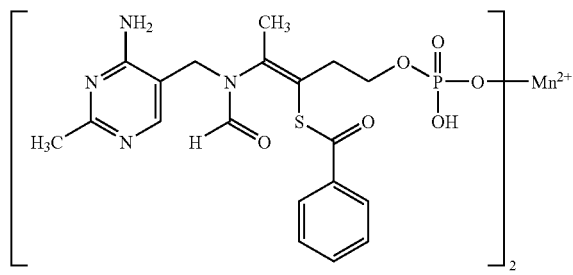

Manganese Benfotiamine

The examples of said manganese complexes include manganese urocanate, manganese urocanate glycinate, manganese urocanate gluconate, manganese adenosine triphosphate, manganese adenosine diphosphate, manganese adenosine mono-phosphate, manganese adenosine triphosphate glycinate, manganese adenosine triphosphate amino acetate, manganese adenosine diphosphate amino acetate, manganese adenosine mono-phosphate amino acetate, manganese benfotiamine glycinate, manganese benfotiamine, manganese benfotiamine amino acetate, manganese benfotiamine gluconate, and combinations thereof.

It is well known that catalases are responsible for the decomposition of peroxides, such as hydrogen peroxide, to water and oxygen. Catalases contain four porphyrin heme (iron) groups. There are no topically known catalases, however. The accumulation of hydrogen peroxide on skin is thus dangerous for human health. The catalase-type decomposition of topical hydrogen peroxide by manganese complexes of the present invention is thus both unexpected and surprising. Although the mechanism of this action is not fully known yet, it is postulated that both manganese and a heterocyclic nitrogen atoms are responsible for a five-center transition state for the decomposition of two moles of hydrogen peroxide to two moles of water and an oxygen molecule via a catalytic mechanism shown in [FIG. 6].

Fig. 6. Catalaze Mimetic Decomposition of Peroxide By Manganese Complexes

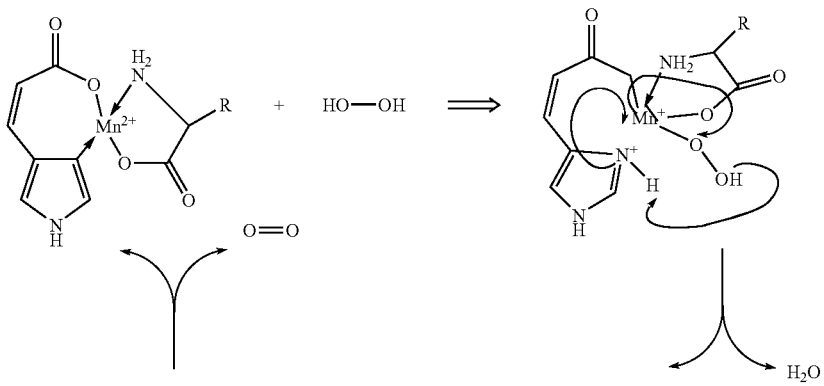

-continued

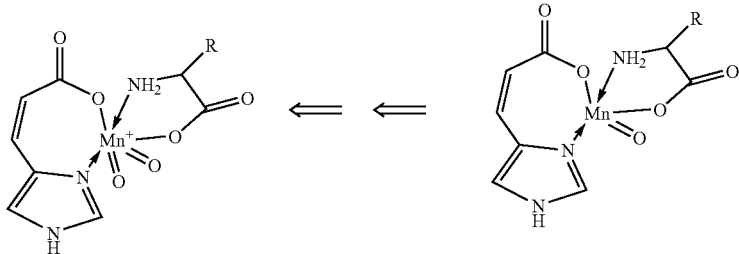

Since it is well known that urocanic acid is present on skin surface in sufficient quantities, the present invention also discloses a novel and simple method for the formation of manganese urocanate complexes via in-situ conversion of said urocanic acid by its contact with manganese complexes of certain nucleotide bases, such as those exemplified in [FIG. 6], which includes manganese adenosine triphosphate, manganese adenosine diphosphate, manganese adenosine monophosphate, manganese adenosine triphosphate glycinate, manganese adenosine triphosphate amino acetate, manganese adenosine diphosphate amino acetate, manganese adenosine mono-phosphate amino acetate, manganese benfotiamine glycinate, manganese benfotiamine, manganese benfotiamine amino acetate, manganese benfotiamine gluconate, EUK-134 [((N,N'-bis(3-methoxysalicylidene)ethylenediamine)) Manganese chloride)], and combinations thereof.

In a yet another surprising discovery, the manganese urocanate complexes of the present invention also cause a skin soothing effect via their reduction of topical hydrogen peroxide. The exact mechanism of this benefit is still unknown. It is possible that the reduction of peroxides can also reduce the formation of other peroxides on skin that may be inflammatory. This anti-inflammatory effect of the manganese urocanate complexes of the present invention is unprecedented. This soothing effect is also useful for both prevention and treatment of sunburn. The present disclosure is both unexpected and surprising in view of Kammeijer et al. (U.S. Pat. No. 7,056,938) who have disclosed that urocanic acid actually causes irritation due to its immunosuppression effect on skin.

The amount of manganese complexes of present invention in a composition can be from catalytic amounts, for example 0.0001 percent, to any desired higher amount. These manganese complexes can be immobilized on a polymer matrix, such as polypore, or on porous surfaces, such as zeolites, silicates, or aluminates.

Urocanates and their various applications have been known for a while.

Gers-Barlag et al. (U.S. Pat. No. 5,658,556) have disclosed hydrophobicized, pharmaceutically or cosmetically acceptable inorganic pigments in cosmetic or dermatological preparations for preventing leaching out or washing off of the skin's cis- or trans-urocaninic acid from the human skin, caused by the action of water, or leaching out or washing off of cis- or trans-urocaninic acid which has been applied artificially to the skin, from the human skin caused by the action of water.

Kim et al. (KR890000113B) disclose a method for preparing uv absorbent powder comprises (i) dispersing inorganic or organic powder, for example, TiO2, kaolin, silk powder, mica, acryl powder into water, (ii) dissolving multivalent metal salt such as Al2(SO4)3 18H2O to adsorb Al (III) ion onto powder surface, (iii) adding uv absorbent such as Na salt of N,N-dimethyl-p-amino-benzoic acid, N,N-dihydroxypropyl-p-amino-benzoic acid or urocanic acid and (iv) washing with water, centrifugally separating and drying.

Kammeijer et al. (EP 1196219) disclose UV absorbing benefits of trans-urocanic acid.

Gers-Barlag et al. (U.S. Pat. No. 6,372,199) disclose use of one or more unsymmetrically substituted s-triazine derivatives in cosmetic or dermatological preparations for preventing the washing out or washing off, caused by the action of water, of endogenous skin cis- and trans-urocanic acid from human skin or the washing out or washing off, caused by the action of water, of cis- and trans-urocanic acid applied artificially to the skin from human skin.

Takanabe et al. (JP 8059446) disclose a two-phase type UV rays protective cosmetic containing an oily UV absorbent, oil-absorbing powder and an aqueous medium. The oily UV absorbent contains an aminobenzoate-based, salicylate-based, cinnamate-based, benzophenone-based or urocanic acid-based ultraviolet absorbent or vitamins. The oil absorbing powder contains an oil absorbing powder. The oil-absorbing powder is composed of a natural organic polymer, a synthetic organic polymer or a natural organic polymer or a complex of the synthetic organic polymer with an inorganic compound. Takanabe et al. do not disclose any peroxide decomposing or SPF enhancing benefits of their compositions. The use of urocanic acid in Takanabe disclosure appears to be for its UV absorbing benefits only.

Sauermann et al. (WO 9420065) disclose the use of an effective quantity of trans-urocanic acid as an antioxidant, optionally in a suitable galenical carrier, for cosmetic and/or dermatological purposes, as well as the use of an effective concentration of trans-urocanic acid as an antioxidant in cosmetic and dermatological formulations.

Diesel et al. (DE 4122497) disclose a composition for external application and treatment (in conjunction with UV irradiation) of inflammatory skin diseases comprises (1) incorporating trans-urocaninic acid (1) into a carrier material, then (2), either on the body surface or in vitro, irradiating the composition with UV light. (I) is thus converted to cis-urocaninic acid (II) which has immunosuppressant activity on cytotoxic lymphocytes. The process is used to treat or prevent psoriasis. Diesel et al. do not disclose any peroxide reducing benefits of their compositions.

Furantsu et al. (JP 4230321) disclose a dermatological composition for treatment and prophylaxis of inflammatory dermatoses and care and restoration of sensitive and stressed skin, which comprises an effective amount of cis-urocanic acid and/or its derivative.

Yamamoto et al. (JP 1117868) disclose urocanic acid derivatives useful as UV absorbers.

The preparation of manganese complexes of nitrogen heterocyclic bases of the present invention can be very simple. In most cases, the mixing of an ammonium, alkali metal, or alkaline earth metal salt of a nitrogen heterocyclic carboxylic acid or phosphoric acid with a manganese donor agent, which can be an organic or an inorganic donor agent, results in the formation of said manganese complexes. Various in-situ processes can also achieve the preparation of said manganese complexes. Certain other complexes, such as EUK-134, may require a more sophisticated manufacturing process.

The sunscreen component of the compositions of the present invention is selected from a large number of such sunscreen and sun-block agents available today that includes zinc oxide, galanga extract, titanium dioxide, PABA, Avobenzone, 3-Benzylidene camphor, Benzylidene camphor sulfonic acid, Bisymydazilate, Camphor Benzalkonium Methosulfate, Polyquaternium-59, Cinnamidipropyltrimonium chloride, Diethylamino hydroxybenzoyl hexyl benzoate, Diethylhexyl butamido triazone, Dimethicodiethylbenzal malonate, Drometrizole trisiloxane, Ecamsule, Ensulizole, Homosalate, Isoamyl p-methoxycinnamate, 4-Methylbenzylidene camphor, Octocrylene, Octyl Dimethyl PABA, Cinoxate, Dioxybenzone, Octyl methoxycinnamate, Octyl salicylate, Octyl triazone, Oxybenzone, PEG-25 PABA, Polyacrylamidomethyl benzylidene camphor, Sulisobenzone, Methyl anthranilate, Trolamine salicylate, Benzophenone-3, Benzophenone-4, Tinosorb M, Tinosorb S, and mixtures thereof.

Certain sunscreen compositions disclosed earlier by the present inventor (U.S. patent application Pre-grant publication No. 20050276761; which corresponds to U.S. patent application Ser. No. 10/710,011, filed Jun. 11, 2004), when used in combination with manganese complexes of the present invention provide greatly improved skin protection from UV and peroxide including hydrogen peroxide. This is further illustrated in Examples 14 to 17.

For topical application to the skin, the compositions of the present invention may be provided in any cosmetic or pharmaceutical form normally used in the cosmetics and dermatological fields, and it may in particular be in the form of an aqueous, optionally gelled, solution, of a dispersion of the optionally two-phase lotion type, of an emulsion obtained by dispersion of a fatty phase (oil) in an aqueous phase (O/W) or vice versa (W/O), of a triple emulsion (W/O/W or O/W/O) or of a vesicular dispersion of the ionic and/or nonionic type. These compositions may be prepared according to the usual methods. This composition may be more or less fluid and have the appearance of a cream, an ointment, a milk, a lotion, a serum, a paste, a powder, and a mousse. It may optionally be applied in the form of an aerosol. It may also be provided in solid form, in particular in the form of a stick. It may be used as a care product and/or as a make-up product for the skin. It may also be used as a shampoo or a conditioner.

The compositions of the present invention can be formulated in various cosmetic and pharmaceutical consumer products utilizing a variety of delivery systems and carrier bases. Such consumer product forms include the group consisting of shampoos, aftershaves, sunscreens, body and hand lotions, skin creams, liquid soaps, bar soaps, bath oil bars, shaving creams, conditioners, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, conditioners, hair lighteners, coloring and non-coloring hair rinses, hair grooming aids, hair tonics, spritzes, styling waxes, band-aids, and balms.

In another preferred aspect, the delivery system can be traditional water and oil emulsions, suspensions, colloids, micro emulsions, clear solutions, suspensions of nanoparticles, emulsions of nanoparticles, or anhydrous compositions.

The compositions of the present invention may also contain adjuvants which are used in the cosmetics field, such as hydrophilic or lipophilic gelling agents, hydrophilic or lipophilic active agents, preserving agents, antioxidants, solvents, fragrances, fillers, screening agents, pigments, odor absorbers and dyestuffs. The amounts of these various adjuvants may be those conventionally used in the field considered. These adjuvants, depending on their nature, can be introduced into the fatty phase, into the aqueous phase or into the lipid vesicles. In addition, moisturizers may complete the effect obtained using the sapogenins according to the invention and anti-inflammatory agents are also useful.

Additional cosmetically or pharmaceutically beneficial ingredients can also be included in the compositions of the present invention, which can be selected from skin cleansers, cationic, anionic surfactants, non-ionic surfactants, amphoteric surfactants, and zwitterionic surfactants, skin and hair conditioning agents, vitamins, hormones, minerals, plant extracts, anti-inflammatory agents, collagen and elastin synthesis boosters, UVA/UVB sunscreens, concentrates of plant extracts, emollients, moisturizers, skin protectants, humectants, silicones, skin soothing ingredients, antimicrobial agents, antifungal agents, treatment of skin infections and lesions, blood microcirculation improvement, skin redness reduction benefits, additional moisture absorbents, analgesics, skin penetration enhancers, solubilizers, moisturizers, emollients, anesthetics, colorants, perfumes, preservatives, seeds, broken seed nut shells, silica, clays, beads, luffa particles, polyethylene balls, mica, pH adjusters, processing aids, and combinations thereof.

In another preferred aspect, the cosmetically acceptable composition further comprises one or more excipient selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, fatty alcohols, ethoxylated fatty alcohols and di-tail phospholipids.

Representative saccharides include nonionic or cationic saccharides such as agarose, amylopectins, amyloses, arabinans, arabinogalactans, arabinoxylans, carageenans, gum arabic, carboxymethyl guar gum, carboxymethyl(hydroxypropyl) guar gum, hydroxyethyl guar gum, carboxymethyl cellulose, cationic guar gum, cellulose ethers including methyl cellulose, chondroitin, chitins, chitosan, chitosan pyrrolidone carboxylate, chitosan glycolate chitosan lactate, cocodimonium hydroxypropyl oxyethyl cellulose, colominic acid ([poly-N acetyl-neuraminic acid]), corn starch, curdlan, dermatin sulfate, dextrans, furcellarans, dextrans, cross-linked dextrans, dextrin, emulsan, ethyl hydroxyethyl cellulose, flaxseed saccharide (acidic), galactoglucomannans, galactomannans, glucomannans, glycogens, guar gum, hydroxy ethyl starch, hydroxypropyl methyl cellulose, hydroxy ethyl cellulose, hydroxy propyl cellulose, hydroxypropyl starch, hydroxypropylated guar gums, gellan gum, gellan, gum ghatti, gum karaya, gum tragancanth (tragacanthin), heparin, hyaluronic acid, inulin, keratin sulfate, konjac mannan, modified starches, laminarans, laurdimonium hydroxypropyl oxyethyl cellulose, okra gum, oxidized starch, pectic acids, pectin, polydextrose, polyquaternium-4, polyquaternium-10, polyquaternium-28, potato starch, protopectins, psyllium seed gum, pullulan, sodium hyaluronate, starch diethylaminoethyl ether, steardimonium hydroxyethyl cellulose, raffinose, rhamsan, tapioca starch, whelan, levan, scleroglucan, sodium alginate, stachylose, succinoglycan, wheat starch, xanthan gum, xylans, xyloglucans, and mixtures thereof. Microbial saccharides can be found in Kirk-Othmer Encyclopedia of Chemical Technology, Fourth Edition, Vol. 16, John Wiley and Sons, NY pp. 578-611 (1994), which is incorporated entirely by reference. Complex carbohydrates found in Kirk-Othmer Encyclopedia of Chemical Technology, Fourth Edition, Vol: 4, John Wiley and Sons, NY pp. 930-948, 1995 which is herein incorporated by reference.

The cosmetically acceptable composition of the present invention may include surface-active agents. Surface-active agents include surfactants, which typically provide detersive functionality to a formulation or act simply as wetting agents. Surface-active agents can generally be categorized as anionic surface-active agents, cationic surface-active agents, nonionic surface-active agents, amphoteric surface-active agents and zwitterionic surface-active agents, and dispersion polymers. Anionic surface-active agents useful herein include those disclosed in U.S. Pat. No. 5,573,709, incorporated herein by reference. Examples include alkyl and alkyl ether sulfates. Specific examples of alkyl ether sulfates which may be used In this invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide. Another suitable class of anionic surface-active agents is the alkyl sulfuric acid salts. Important examples are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, for example, sulfur trioxide or oleum, obtained according to known sulfonation methods, including bleaching and hydrolysis. Preferred are alkali metals and ammonium sulfated $C_{12-38}$ n-paraffins.

Additional synthetic anionic surface-active agents include the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Preferred anionic surface-active agents for use in the cosmetically acceptable composition of present invention include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric surface-active agents which may be used in the cosmetically acceptable composition of present invention include derivatives of aliphatic secondary and tertiary amines, in which the aliphatic substituent contains from about 8 to 18 carbon atoms and an anionic water solubilizing group e.g., carboxy, sulfonate, sulfate, phosphate, or phosphonate. Representative examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate as described in U.S. Pat. No. 2,658,072, N-higher alkyl aspartic acids as described in U.S. Pat. No. 2,438,091, and the products sold under the trade name MIRANOL. as described in U.S. Pat. No. 2,528,378. Other sarcosinates and sarcosinate derivatives can be found in the CTFA Cosmetic Ingredient Handbook, Fifth Edition, 1988, page 42 incorporated herein by reference.

Quaternary ammonium compounds can also be used in the cosmetically acceptable composition of the present invention as long as they are compatible in the compositions of the invention, wherein the structure is provided in the CTFA Cosmetic Ingredient Handbook, Fifth Edition, 1988, page 40. Cationic surface-active agents generally include, but are not limited to fatty quaternary ammonium compounds containing from about 8 to about 18 carbon atoms. The anion of the quaternary ammonium compound can be a common ion such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, hydrogen, benzyl or short chain alkyl or hydroxyalkyl groups such as methyl, ethyl, hydroxymethyl or hydroxyethyl, hydroxypropyl or combinations thereof.

Examples of quaternary ammonium compounds include but are not limited to; Behentrimonium chloride, Cocotrimonium chloride, Cethethyldimonium bromide, Dibehenyldimonium chloride, Dihydrogenated tallow benzylmonium chloride, disoyadimonium chloride, Ditallowedimonium chloride, Hydroxycetyl hydroxyethyl dimonium chloride, Hydroxyethyl Behenamidopropyl dimonium chloride, Hydroxyethyl Cetyldimonium chloride, Hydroxyethyl tallowedimonium chloride, myristalkonium chloride, PEG-2 Oleamonium chloride, PEG-5 Stearmonium chloride, PEG-15 cocoyl quaternium 4, PEG-2 stearalkonium 4, lauryltrimonium chloride; Quaternium-16; Quaternium-18, lauralkonium chloride, olealkmonium chloride, cetylpyridinium chloride, Polyquaternium-5, Polyquaternium-6, Polyquaternium-7, Polyquaternium-10, Polyquaternium-22, Polyquaternium-37, Polyquaternium-39, Polyquaternium-47, cetyl trimonium chloride, dilauryidimonium chloride, cetalkonium chloride, dicetyldimonium chloride, soyatrimonium chloride, stearyl octyl dimonium methosulfate, and mixtures thereof. Other quaternary ammonium compounds are listed in the CTFA Cosmetic Ingredient Handbook, First Edition, on pages 41-42, incorporated herein by reference.

The cosmetically acceptable compositions of the present invention may include long chain fatty amines from about $C_{10}$ to $C_{22}$ and their derivatives. Specific examples include dipalmitylamine, lauramidopropyldimethylamine, and stearamidopropyl dimethylamine. The cosmetically acceptable compositions of this invention may also include fatty alcohols (typically monohydric alcohols), ethoxylated fatty alcohols, and di-tail phospholipids, which can be used to stabilize emulsion or dispersion forms of the cosmetically acceptable compositions. They also provide a cosmetically acceptable viscosity. Selection of the fatty alcohol is not critical, although those alcohols characterized as having fatty chains of $C_{10}$ to $C_{32}$, preferably $C_{14}$ to $C_{22}$, which are substantially saturated alkanols will generally be employed. Examples include stearyl alcohol, cetyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols, preferably with stearyl alcohol. When used the fatty alcohol is preferably included in the formulations of this invention at a concentration within the range from about 1 to about 8 weight percent, more preferably about 2 to about 6 weight percent. The fatty alcohols may also be ethoxylated. Specific examples include cetereth-20, steareth-20, steareth-21, and mixtures thereof. Phospholipids such as phosphatidylserine and phosphatidylcholine, and mixtures thereof may also be included. When used, the fatty alcohol component is included in the formulations at a concentration of about 1 to about 10 weight percent, more preferably about 2 to about 7 weight percent.

Nonionic surface-active agents, which can be used in the cosmetically acceptable composition of the present invention, include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; the polyethylene glycol (PEG) glyceryl fatty esters.

Zwitterionic surface-active agents such as betaines can also be useful in the cosmetically acceptable composition of this invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl)carboxymethyl betaine, oleyl dimethyl gamma-carboxypropyl betaine, and lauryl bis-(2-hydroxypropyl)alphacarboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH $(CH_2)_3$ radical is attached to the nitrogen atom of the betaine are also useful in this invention.

The anionic, cationic, nonionic, amphoteric or zwitterionic surface-active agents used in the cosmetically acceptable composition of the present invention are typically used in an amount from about 0.1 to 50 percent by weight, preferably from about 0.5 to about 40 percent by weight, more preferably from about 1 to about 20 percent by weight.

The cosmetically acceptable compositions of the present invention may include humectants, which act as hygroscopic agents, increasing the amount of water absorbed, held and retained. Suitable humectants for the formulations of this invention include but are not limited to: acetamide MEA, ammonium lactate, chitosan and its derivatives, colloidal oatmeal, galactoarabinan, glucose glutamate, glerecyth-7, glygeryth-12, glycereth-26, glyceryth-31, glycerin, lactamide MEA, lactamide DEA, lactic acid, methyl gluceth-10, methyl gluceth-20, panthenol, propylene glycol, sorbitol, polyethylene glycol, 1,3-butanediol, 1,2,6-hexanetriol, hydrogenated starch hydrolysate, inositol, mannitol, PEG-5 pentaerythritol ether, polyglyceryl sorbitol, xylitol, sucrose, sodium hyaluronate, sodium PCA, and combinations thereof. Glycerin is a particularly preferred humectant. The humectant is present in the composition at concentrations of from about 0.5 to about 40 percent by weight, preferably from about 0.5 to about 20 percent by weight and more preferably from about 0.5 to about 12 percent by weight.

The cosmetically acceptable compositions of the present invention may include petrolatum or mineral oil components, which when selected will generally be USP or NF grade. The petrolatum may be white or yellow. The viscosity or consistency grade of petrolatum is not narrowly critical. Petrolatum can be partially replaced with mixtures of hydrocarbon materials, which can be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefins, beeswax, synthetic candelilla wax, synthetic carnauba, synthetic beeswax and the like may be blended together. Alkylmethyl siloxanes with varying degrees of substitution can be used to increase water retained by the skin. Siloxanes such as stearyl dimethicone, known as 2503 Wax, C30-45 alkyl methicone, known as AMS-C30 wax, and stearoxytrimethylsilane (and) stearyl alcohol, known as 580 Wax, each available from Dow Corning, Midland, Mich., USA. Additional alkyl and phenyl silicones may be employed to enhance moisturizing properties. Resins such as dimethicone (and) trimethylsiloxysilicate or Cyclomethicone (and) Trimethylsiloxysilicate fluid, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins can be included from about 0.1 to about 10.0 weight percent.

Emollients are defined as agents that help maintain the soft, smooth, and pliable appearance of skin. Emollients function by their ability to remain on the skin surface or in the stratum corneum. The cosmetically acceptable composition of the present invention may include fatty ester emollients, which are listed in the International Cosmetic Ingredient Dictionary, Eighth Edition, 2000, p. 1768 to 1773. Specific examples of suitable fatty esters for use in the formulation of this invention include isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, PPG-5-Ceteth-20, 2-ethylhexyl isononoate, 2-ethylhexyl stearate, $C_{12}$ to $C_{16}$ fatty alcohol lactate, isopropyl lanolate, 2-ethyl-hexyl salicylate, and mixtures thereof. The presently preferred fatty esters are isopropyl myristate, isopropyl palmitate, PPG-5-Ceteth-20, and caprylic/capric triglycerides. When used the fatty ester emollient is preferably included in the formulations of this invention at a concentration of about 1 to about 8 weight percent, more preferably about 2 to about 5 weight percent.

The compositions of the present invention may also include silicone compounds. Preferably, the viscosity of the silicone component is from about 0.5 to about 12,500 cps. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone, a dimethylpolysiloxane end-blocked with trimethyl units, is one preferred example. Dimethicone having a viscosity between 50 and 1,000 cps is particularly preferred. When used, the silicone oils are preferably included in the formulations of this invention at a concentration of 0.1 to 5 weight percent, more preferably 1 to 2 weight percent.

The cosmetically acceptable compositions of the present invention may include volatile and non-volatile silicone oils or fluids. The silicone compounds can be either linear or cyclic polydimethylsiloxanes with a viscosity from about 0.5 to about 100 centistokes. The most preferred linear polydimethylsiloxane compounds have a range from about 0.5 to about 50 centistokes. One example of a linear, low molecular weight, volatile polydimethylsiloxane is octamethyltrisiloxane. 200 fluid having a viscosity of about 1 centistoke. When used, the silicone oils are preferably included in the formulations of this invention at a concentration of 0.1 to 30 weight percent, more preferably 1 to 20 weight percent.

The cosmetically acceptable compositions of the present invention may include volatile, cyclic, low molecular weight polydimethylsiloxanes (cyclomethicones). The preferred cyclic volatile siloxanes can be polydimethyl cyclosiloxanes having an average repeat unit of 4 to 6, and a viscosity from about 2.0 to about 7.0 centistokes, and mixtures thereof. Preferred cyclomethicones are available from Dow Corning, Midland, Mich., and from General Electric, Waterford, N.Y., USA. When used, the silicone oils are preferably included in the formulations of this invention at a concentration of 0.1 to 30 weight percent, more preferably 1 to 20 weight percent.

Silicone surfactants or emulsifiers with polyoxyethylene or polyoxypropylene side chains may also be used in compositions of the present invention. Preferred examples include dimethicone copolyols and 5225C Formulation Aids, available from Dow Corning, Midland, Mich., USA and Silicone SF-1528, available from General Electric, Waterford, N.Y., USA. The side chains may also include alkyl groups such as lauryl or cetyl. Preferred are lauryl methicone copolyol. 5200 Formulation Aid, and cetyl dimethicone copolyol, known as Abil EM-90, available from Goldschmidt Chemical Corporation, Hopewell, Va. Also preferred is lauryl dimethicone, known as Belsil LDM 3107 VP, available from Wacker-Chemie, Munchen, Germany. When used, the silicone surfactants are preferably included in the formulations of this invention at a concentration of 0.1 to 30 weight percent, more preferably 1 to 15 weight percent. Amine functional silicones and emulsions may be utilized in the present invention. Preferred examples include Dow Corning 8220, Dow Corning 939, Dow Corning 949, Dow Corning 2-8194, all available from Dow Corning, Midland, Mich., USA. Also preferred is Silicone SM 253 available from General Electric, Waterford, N.Y., USA. When used, the amine functional silicones are preferably included in the formulations of this invention at a concentration of 0.1 to 5 weight percent, more preferably 0.1 to 2.0 weight percent.

[The cosmetically acceptable compositions of the present invention may include volatile hydrocarbon oils. The volatile hydrocarbon comprises from about $C_6$ to $C_{22}$ atoms. A preferred volatile hydrocarbon is an aliphatic hydrocarbon having a chain length from about $C_6$ to $C_{16}$ carbon atoms. An example of such compound includes isohexadecane, under the trade name Permethyl 101A, available from Presperse, South Plainfield, N.J., USA. Another example of a preferred volatile hydrocarbon is $C_{12}$ to $C_{14}$ isoparaffin, under the trade name Isopar M, available from Exxon, Baytown, Tex., USA. When used, the volatile hydrocarbons are preferably included in the formulations of this invention at a concentration of 0.1 to 30 weight percent, more preferably 1 to 20 weight percent.

The cosmetically acceptable compositions of the present invention may include cationic and ampholytic conditioning polymers. Examples of such include, but are not limited to those listed by the International Cosmetic Ingredient Dictionary published by the Cosmetic, Toiletry, and Fragrance Association (CTFA), 1101 17 Street, N.W., Suite 300, Washington, D.C. 20036. General examples include quaternary derivatives of cellulose ethers, quaternary derivatives of guar, homopolymers and copolymers of DADMAC, homopolymers and copolymers of MAPTAC and quaternary derivatives of starches. Specific examples, using the CTFA designation, include, but are not limited to Polyquaternium-10, Guar hydroxypropyltrimonium chloride, Starch hydroxypropyltrimonium chloride, Polyquaternium-4, Polyquaternium-5, Polyquaternium-6, Polyquaternium-7; Polyquaternium-14, Polyquaternium-15, Polyquaternium-22, Polyquaternium-24, Polyquaternium-28, Polyquaternium-32, Polyquaternium-33, Polyquaternium-36, Polyquaternium-37, Polyquaternium-39, Polyquaternium-45, Polyquaternium-47 and polymethacrylamidopropyltrimonium chloride, and mixtures thereof. When used, the conditioning polymers are preferably included in the cosmetically acceptable composition of this invention at a concentration of from 0.1 to 10 weight percent, preferably from 0.2 to 6 weight percent and most preferably from 0.2 to 5 weight percent.

The cosmetically acceptable compositions of the present invention may include one or more rheological modifiers. The rheological modifiers that can be used in this invention include, but are not limited to high molecular weight crosslinked homopolymers of acrylic acid, and Acrylates/C10-30 Alkyl Acrylate Crosspolymer, such as the Carbopol. and Pemulen series, both available from B. F. Goodrich, Akron, Ohio, USA; anionic acrylate polymers such as Salcare and cationic acrylate polymers such as Salcare SC96, available from Ciba Specialties, High Point, N.C., USA; Acrylamidopropylttrimonium chloride/acrylamide; Hydroxyethyl methacrylates polymers, Steareth-10 Allyl Ether/Acrylate Copolymer; Acrylates/Beheneth-25 Metacrylate Copolymer, known as Aculyn, available from International Specialties, Wayne, N.J., USA; Glyceryl Polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof. When used, the rheology modifiers are preferably included in the cosmetically acceptable composition of this invention at a concentration of from 0.01 to 12 weight percent, preferably from 0.05 to 10 weight percent and most preferably from 0.1 to 6 weight percent.

The cosmetically acceptable composition of the present invention may include one or more antioxidants, which include, but are not limited to ascorbic acid, BHT, BHA, erythorbic acid, bisulfite, thioglycolate, tocopherol, sodium metabisulfite, vitamin E acetate, and ascorbyl palmitate. The anti oxidants will be present at from 0.01 to 5 weight percent, preferably 0.1 to 3 weight percent and most preferably from 0.2 to 2 weight percent of the cosmetically acceptable composition.

The cosmetically acceptable compositions of the present invention may include one or more additional sunscreen active agents. Examples of sunscreen active agents include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis (hydroxypropyl) aminobenzoate, 2-ethylhexy 1-2-cyano-3,3-diphenylacrylate, homomethyl salicylate, glyceryl aminobenzoate, dihydroxyacetone, octyl dimethyl PABA, 2-phenylbenzimidazole-5-sulfonic acid, triethanolamine salicylate, zinc oxide, titanium oxide, zinc zeolite, titanium zeolite, and mixtures thereof. The amount of sunscreen used in the cosmetically acceptable composition of this invention will vary depending on the specific UV absorption wavelength(s) of the specific sunscreen active(s) used, or to meet certain governmental regulatory requirements of a specific country or place.

The cosmetically acceptable compositions of the present invention may include one or more preservatives. Example of preservatives, which may be used include, but are not limited to 1,2-dibromo-2,4-dicyano butane (Methyldibromo Glutaronitrile, known as MERGUARD. Nalco Chemical Company, Naperville, Ill., USA), benzyl alcohol, imidazolidinyl urea, 1,3-bis(hydroxymethyl)-5,5-dimethyl-2,3-imidazolidinedione (e.g., DMDM Hydantoin, known as GLYDANT, Lonza, Fairlawn, N.J., USA.), methylchloroisothiazolinone and methylisothiazolinone (e.g., Kathon, Rohm & Haas Co., Philadelphia, Pa., USA), methyl paraben, propyl paraben, phenoxyethanol, Chlorphenesin, usnic acid, natamycin, sodium benzoate, and mixtures thereof.

The cosmetically acceptable compositions of the present invention may include any other ingredient by normally used in cosmetics. Examples of such ingredients include, but are not limited to buffering agents, fragrance ingredients, chelating agents, color additives or dyestuffs which can serve to color the composition itself or keratin, sequestering agents, softeners, foam synergistic agents, foam stabilizers, sun filters and peptizing agents.

The surface of pigments, such titanium dioxide, zinc oxide, talc, calcium carbonate or kaolin, can be treated with the unsaturated quaternary ammonium compounds described herein and then used in the cosmetically acceptable composition of the present invention. The treated pigments are then more effective as sunscreen actives and for use in color cosmetics such as make up and mascara.

The cosmetically acceptable compositions of the present invention can be presented in various forms. Examples of such forms include, but are not limited a solution, liquid, cream, emulsion, dispersion, gel, thickening lotion.

The cosmetically acceptable compositions of the present invention may contain water and also any cosmetically acceptable solvent. Examples of acceptable solvents include, but are not limited to monoalcohols, such as alkanols having 1 to 8 carbon atoms (like ethanol, isopropanol, benzyl alcohol and phenylethyl alcohol) polyalcohols, such as alkylene glycols (like glycerine, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture. These solvents can be present in proportions of up to as much as 70 percent by weight, for example from 0.1 to 70 percent by weight, relative to the weight of the total composition.

The cosmetically acceptable compositions of the present invention can also be packaged as an aerosol, in which case it can be applied either in the form of an aerosol spray or in the form of an aerosol foam. As the propellant gas for these aerosols, it is possible to use, in particular, dimethyl ether, carbon dioxide, nitrogen, nitrous oxide, air and volatile hydrocarbons, such as butane, isobutane, and propane.

The cosmetically acceptable compositions of the present invention can contain electrolytes, such as aluminum chlorohydrate, aluminum zirconium chlorohydrate, alkali metal salts, e.g., sodium, potassium or lithium salts, these salts preferably being halides, such as the chloride or bromide, and the sulfate, or salts with organic acids, such as the acetates or lactates, and also alkaline earth metal salts, preferably the carbonates, silicates, nitrates, acetates, gluconates, pantothenates and lactates of calcium, magnesium and strontium.

Compositions of the present invention can include leave-on or rinse-off skin care products such as lotions, hand/body creams, shaving gels or shaving creams, body washes, sunscreens, liquid soaps, deodorants, antiperspirants, suntan lotions, after sun gels, bubble baths, hand or mechanical dishwashing compositions, and the like. In addition to the polymer, skin care compositions may include components conventionally used in skin care formulations. Such components include for example; (a) humectants, (b) petrolatum or mineral oil, (c) fatty alcohols, (d) fatty ester emollients, (e) silicone oils or fluids, and (f) preservatives. These components must in general be safe for application to the human skin and must be compatible with the other components of the formulation. Selection of these components is generally within the skill of the art. The skin care compositions may also contain other conventional additives employed in cosmetic skin care formulations. Such additives include aesthetic enhancers, fragrance oils, dyes and medicaments such as menthol and the like.

The skin care compositions of the present invention may be prepared as oil-in-water, water-in-oil emulsions, triple emulsions, or dispersions.

Preferred oil-in-water emulsions are prepared by first forming an aqueous mixture of the water-soluble components, e.g. unsaturated quaternary ammonium compounds, humectants, water-soluble preservatives, followed by adding water-insoluble components. The water-insoluble components include the emulsifier, water-insoluble preservatives, petrolatum or mineral oil component, fatty alcohol component, fatty ester emollient, and silicone oil component. The input of mixing energy will be high and will be maintained for a time sufficient to form a water-in-oil emulsion having a smooth appearance (indicating the presence of relatively small micelles in the emulsion). Preferred dispersions are generally prepared by forming an aqueous mixture of the water-soluble components, followed by addition of thickener with suspension power for water-insoluble materials.

Compositions of the present invention for treating hair include bath preparations such as bubble baths, soaps, and oils, shampoos, conditioners, hair bleaches, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products. The dispersion polymers may also be utilized in styling type leave-in products such as gels, mousses, spritzes, styling creams, styling waxes, pomades, balms, and the like, either alone or in combination with other polymers or structuring agents in order to provide control and hair manageability with a clean, natural, non-sticky feel.

Hair care compositions of the present invention give slippery feel and that can be easily rinsed from the hair due to the presence of the dispersion polymer, volatile silicones, other polymers, surfactants or other compounds that may alter the deposition of materials upon the hair.

In the case of cleansing formulations such as a shampoo for washing the hair, or a liquid hand soap, or shower gel for washing the skin, the compositions of the present invention contain anionic, cationic, nonionic, zwitterionic or amphoteric surface-active agents typically in an amount from about 3 to about 50 percent by weight, preferably from about 3 to about 20-percent, and their pH is general in the range from about 3 to about 10.

Preferred shampoos of the present invention contain combinations of anionic surfactants with zwitterionic surfactants and/or amphoteric surfactants. Especially preferred shampoos contain from about 0 to about 16 percent active of alkyl sulfates, from 0 to about 50 weight percent of ethoxylated alkyl sulfates, and from 0 to about 50 weight percent of optional surface-active agents selected from the nonionic, amphoteric, and zwitterionic surface-active agents, with at least 5 weight percent of either alkyl sulfate, ethoxylated alkyl sulfate, or a mixture thereof, and a total surfactant level of from about 10 weight to about 25 percent.

The shampoo for washing hair also can contain other conditioning additives such as silicones and conditioning polymers typically used in shampoos. U.S. Pat. No. 5,573,709 provides a list of non-volatile silicone conditioning agents that can be used in shampoos. The conditioning polymers for use with the present invention are listed in the Cosmetic, Toiletries and Fragrance Associations (CTFA) dictionary. Specific examples include the Polyquaterniums (example Polyquaternium-1 to Polyquaternium-50), Guar Hydroxypropyl Trimonium Chloride, Starch Hydroxypropyl Trimonium Chloride and Polymethacrylamidopropyl Trimonium Chloride.

Other preferred embodiments consist of use in the form of a rinsing lotion to be applied mainly before or after shampooing. These lotions typically are aqueous or aqueous-alcoholic solutions, emulsions, thickened lotions or gels. If the compositions are presented in the form of an emulsion, they can be nonionic, anionic or cationic. The nonionic emulsions consist mainly of a mixture of oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions of the present invention are presented in the form of a thickened lotion or a gel, they contain thickeners in the presence or absence of a solvent. The thickeners which can be used are especially resins, Carbopol-type acrylic acid thickeners available from B.F. Goodrich; xanthan gums; sodium alginates; gum arabic; cellulose derivatives and poly-(ethylene oxide) based thickeners, and it is also possible to achieve thickening by means of a mixture of polyethylene glycol stearate or distearate or by means of a mixture of a phosphoric acid ester and an amide. The concentration of thickener is generally 0.05 to 15 percent by weight. If the compositions are presented in the form of a styling lotion, shaping lotion, or setting lotion, they generally comprise, in aqueous, alcoholic or aqueous-alcoholic solution, the ampholyte polymers defined above.

In the case of hair fixatives, the composition of the present invention may also contain one or more additional hair fixative polymers. When present, the additional hair fixative polymers are present in a total amount of from about 0.25 to about 10 percent by weight. The additional hair fixative resin can be selected from the following group as long as it is compatible with a given dispersion polymer: acrylamide copolymer, acrylamide/sodium acrylate copolymer, acrylate/ammonium methacrylate copolymer, an acrylate copolymer, an acrylic/acrylate copolymer, ad ipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, an ammonium acrylate copolymer, an ammonium vinyl acetate/acrylate copolymer, an AMP acrylate/diacetoneacrylamide copolymer, an AMPD acrylate/diacetoneacrylamide copolymer, butyl ester of ethylene/maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine-copolymer, dodecanedioic acid/cetearyl alcohol/glycol copolymer, ethyl ester of PVM/MA copolymer, isopropyl ester of PVM/MA copolymer, karaya gum, a methacryloyl ethyl betaine/methacrylate copolymer, an octylacrylamide/acrylate/butylaminoethyl methacrylate copolymer, an octylacrylamide/acrylate copolymer, phthalic anhydride/glycerin/glycidyl decanoate copolymer, a phthalic/trimellitic/glycol copolymer, polyacrylamide, polyacrylamidomethylpropane sulfonic acid, polybutylene terephthalate, polyethylacrylate, polyethylene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-39, polyquaternium-47, polyvinyl acetate, polyvinyl butyral, polyvinyl imidazolinium acetate, polyvinyl methyl ether, PVM/MA copolymer, PVP, PVP/dimethylaminoethylmethacrylate copolymer, PVP/eicosene copolymer, PVP/ethyl methacrylate/methacrylic acid copolymer, PVP/hexadecene copolymer, PVP/VA copolymer, PVP/vinyl acetate/itaconic acid copolymer, shellac, sodium acrylates copolymer, sodium acrylates/Acrylnitrogens copolymer, sodium acrylate/vinyl alcohol copolymer, sodium carrageenan, starch diethylaminoethyl ether, stearylvinyl ether/maleic anhydride copolymer, sucrose benzoate/sucrose acetate isobutyrate/butyl benzyl phthalate copolymer, sucrose benzoate/sucrose acetate isobutyrate/butyl benzyl phthalate/methyl methacrylate copolymer, sucrose benzoate/sucrose acetate isobutyrate copolymer, a vinyl acetate/crotonate copolymer, vinyl acetate/crotonic acid copolymer, vinyl acetate/crotonic acid/methacryloxybenzophenone-1 copolymer, vinyl acetate/crotonic acid/vinyl neodecanoate copolymer, and mixtures thereof. Synthetic polymers used for creating styling aids are described in "The History of Polymers in Haircare," Cosmetics and Toiletries, 103 (1988), incorporated herein by reference. Other synthetic polymers that may be used with the present invention can be referenced in the CTFA Dictionary, Fifth Edition, 2000, incorporated herein by reference.

The cosmetically acceptable carrier contained in the cosmetic compositions of the present invention may be varied depending on the type of the formulation. For example, the formulation of ointment, pastes, creams or gels may comprise animal and vegetable fats, waxes, paraffins, starch, tragacanth, cellulose derivatives, polyethylene glycols, silicones, bentonites, silica, talc, zinc oxide or mixtures of these ingredients.

In the formulation of powder or spray, it may comprise lactose, talc, silica, aluminum hydroxide, calcium silicate, polyamide powder and mixtures of these ingredients. Spray may additionally comprise the customary propellants, for example, chlorofluorohydrocarbons, propane, butane, diethyl ether, or dimethyl ether.

The formulation of solution and emulsion of the present invention may comprise solvent, solubilizer and emulsifier, for example water, ethanol, isopropanol, ethyl carbonate, ethyl acetate, benzyl alcohol, benzyl benzoate, propylene glycol, 1,3-butyleneglycol, oils, in particular cottonseed oil, groundnut oil, maize germ oil, olive oil, castor oil and sesame seed oil, glycerol fatty esters, polyethylene glycol and fatty acid esters of sorbitan or mixtures of these ingredients.

The formulation of suspension of the present invention may comprise liquid diluents, for example water, ethanol or propylene glycol, suspending agents, for example ethoxylated isosteary alcohols, polyoxyethylene sorbitol esters and poly oxyethylene sorbitan esters, micocrystalline cellulose, aluminum metahydroxide, bentonite, agar and tragacanth or mixtures of these ingredients.

The formulation of cleansing compositions of the present invention with surfactant may comprise aliphatic alcohol sulfate, aliphatic alcohol ether sulfate, sulfosucinnate monoester, isothionate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives, ethoxylated glycerol fatty acid ester or mixtures of these ingredients.

Additional antioxidant ingredients and compositions can be selected from, but not limited to, Ascorbic acid, Ascorbic acid derivatives, Glucosamine ascorbate, Arginine ascorbate, Lysine ascorbate, Glutathione ascorbate, Nicotinamide ascorbate, Niacin ascorbate, Allantoin ascorbate, Creatine ascorbate, Creatinine ascorbate, Chondroitin ascorbate, Chitosan ascorbate, DNA Ascorbate, Carnosine ascorbate, Vitamin E, various Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), a-Lipoic acid, Niacinamide lipoate, Glutathione, Andrographolide (*Andrographis paniculata*), Carnosine, Niacinamide, Potentilla erecta extract, Polyphenols, Grapeseed extract, Pycnogenol (Pine Bark extract), Pyridoxine, Magnolol, Honokiol, Paeonol, Resacetophenone, Quinacetophenone, arbutin, kojic acid, and combinations thereof.

The blood micro-circulation improvement ingredients and compositions can be added to compositions of the present invention. These are selected from Horse Chestnut Extract (*Aesculus hippocastanum* extract)), Esculin, Escin, Yohimbine, *Capsicum* Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), Emblica extract (*Phyllanthus emblica* extract), Asiaticoside (*Centella asiatica* extract), *Boswellia* Extract (*Boswellia serrata*), Ginger Root Extract (*Zingiber Officianalis*), Piperine, Vitamin K, Melilot (*Melilotus officinalis* extract), Glycyrrhetinic acid, Ursolic acid, Sericoside (*Terminalia sericea* extract), Darutoside (*Siegesbeckia orientalis* extract), *Amni visnaga* extract, extract of Red Vine (*Vitis Vinifera*) leaves, apigenin, phytosan, luteolin, and combinations thereof.

The anti-inflammatory ingredients can be added to compositions of the present invention. These can be selected from at least one antioxidant class of Cyclo-oxygenase (for example, COX-1 or COX-2) or Lipoxygenase (for example, LOX-5) enzyme inhibitors such as Ascorbic acid, Ascorbic acid derivatives, Vitamin E, Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), alpha-Lipoic acid, Glutathione, Andrographolide, Grapeseed extract, Green Tea Extract, Polyphenols, Pycnogenol (Pine Bark extract), White Tea extract, Black Tea extract, (*Andrographis paniculata*), Carnosine, Niacinamide, and Emblica extract. Anti-inflammatory composition can additionally be selected from, but not limited to, Horse Chestnut Extract (*Aesculus hippocastanum* extract)), Esculin, Escin, Yohimbine, *Capsicum* Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), Emblica extract (*Phyllanthus emblica* extract), Asiaticoside (*Centella asiatica* extract), *Boswellia* Extract (*Boswellia serrata*), Sericoside, Visnadine, Thiocolchicoside, Grapeseed Extract, Ginger Root Extract (*Zingiber Officianalis*), Piperine, Vitamin K, Melilot (*Melilotus officinalis* extract), Glycyrrhetinic acid, Ursolic acid, Sericoside (*Terminalia sericea* extract), Darutoside (*Siegesbeckia orientalis* extract), *Amni visnaga* extract, extract of Red Vine (Vitis-Vinifera) leaves, apigenin, phytosan, luteolin, and combinations thereof.

Certain divalent metal ions can be added to compositions of the present invention. The examples of such metal ions include zinc, copper, vanadium, chromium, cobalt, selenium, molybdenum, and iron.

EXAMPLES

The following examples are presented to illustrate presently preferred practice thereof. These examples also include the formulation of consumer desirable lotion, cream, and other such compositions for their retail marketing. As illustrations they are not intended to limit the scope of the invention. All quantities are in weight percent.

Example 1

In-Situ Preparation of Manganese (II) Urocanate

Ingredients. (1) Deionized water 96.49 (2) Manganese (II) Acetate 1.73 (3) Urocanic acid 1.38 (4) Sodium Hydroxide 0.4. Procedure. Make main batch by mixing (1), (3), and (4)

at 50 to 60 C. Add (2) and mix. Cool to room temperature. The mixture contains 1.9 percent by weight of Manganese urocanate.

Example 2

In-Situ Preparation of Manganese (III) Urocanate Acetate

Ingredients. (1) Deionized water 95.54 (2) Manganese (III) Acetate Dihydrate 2.68 (3) Urocanic acid 1.38 (4) Sodium Hydroxide 0.4. Procedure. Make main batch by mixing (1), (3), and (4) at 50 to 60 C. Add (2) and mix. Cool to room temperature. The mixture contains 2.5 percent by weight of Manganese (III) urocanate acetate.

Example 3

In-Situ Preparation of Manganese (II) Urocanate

Ingredients. (1) Deionized water 96.79 (2) Manganese (II) Chloride Monohydrate 1.43 (3) Urocanic acid 1.38 (4) Sodium Hydroxide 0.4. Procedure. Make main batch by mixing (1), (3), and (4) at 50 to 60 C. Add (2) and mix. Cool to room temperature. The mixture contains 1.9 percent by weight of Manganese urocanate.

Example 4

In-Situ Preparation of Manganese (II) Urocanate

Ingredients. (1) Deionized water 96.52 (2) Manganese (II) Sulfate 1.7 (3) Urocanic acid 1.38 (4) Sodium Hydroxide 0.4. Procedure. Make main batch by mixing (1), (3), and (4) at 50 to 60 C. Add (2) and mix. Cool to room temperature. The mixture contains 2.5 percent by weight of Manganese (II) urocanate.

Example 5

In-Situ Preparation of Manganese (II) Urocanate Glycinate

Ingredients. (1) Deionized water 95.58 (2) Manganese bis-Glycinate 2.04 (3) Urocanic acid 1.38. Procedure. Mix (1) to (3) at 50 to 60 C. Cool to room temperature. The mixture contains 1 mMol of Manganese (II) urocanate glycinate.

Example 6

In-Situ Preparation of Manganese (II) Adenosine Triphosphate Glycinate

Ingredients. (1) Deionized water 95.58 (2) Manganese bis-Glycinate 2.04 (3) Adenosine Triphosphate, Disodium hydrate 5.51 (anhydrous basis). Procedure. Mix (1) to (3) at 50 to 60 C. Cool to room temperature. The mixture contains 1 mMol of Manganese (II) adenosine triphosphate glycinate.

Example 7

In-Situ Preparation of Manganese (III) Urocanate Methanesulfonate

Ingredients. (1) Deionized water 94.34 (2) Manganese (III) Methanesulfonate 3.88 (3) Urocanic acid 1.38 (4) Sodium Hydroxide 0.4. Procedure. Make main batch by mixing (1), (3), and (4) at 50 to 60 C. Add (2) and mix. Cool to room temperature. The mixture contains 1 mMol of Manganese (III) urocanate methanesulfonate.

Example 8

Peroxide Decomposing Sunscreen Cream

Ingredients. (1) Water 56.9 (2) Dicetyl Phosphate (and) Ceteth-10 Phosphate 5.0 (3) Glyceryl Stearate (and) PEG-100 Stearate 4.0 (4) Phenoxyethanol 0.7 (5) Chlorphenesin 0.3 (60) Titanium Dioxide 0.2 (7) Sodium Hydroxide 0.5 (8) Magnolol 0.2 (9) *Boswellia Serrata* 0.5 (10) Benzophenone-3 4.0 (11) Manganese Urocanate 0.5 (12) Shea butter 2.0 (13) Rosmarinic Acid 1.0 (14) Water 5.0 (15) Octyl methoxycinnamate 5.0 (16) Polyamide-3 3.0 (17) 2,4-Dihydroxy Acetophenone (Resacetophenone) 1.1 (18) Triethyl citrate 1.5 (19) EUK-134 0.1 (20) Cyclomethicone, Dimethicone Crosspolymer 2.0 (21) Zinc Zeolite 2.5 (22) Polysorbate-20 2.0 (23) Sepigel-305 2.0. Procedure. Mix (1) to (22) and heat at 70 to 80 C till homogenous. Cool to 40 to 50 C. Cool to room temperature; add (23) to a desired viscosity. An off-white cream is obtained.

Example 9

Anti-Wrinkle Gel with Facial Peroxide Reduction

Ingredients. (1) Triethyl Citrate 67.00 (2) Ethylenediamine/Hydrogenated Dimer Dilinoleate Copolymer Bis-D1-C14-18 Alkyl Amide 10.0 (3) Ximenia Oil 0.1 (4) Sesamin 1.0 (5) Magnolol (and Honokiol 0.2 (6) Schisandrin 0.5 (7) EUK-134 0.2 (8) Zinc Zeolite 20.0 (9) Fragrance 1.0. Procedure. Mix (1) and (2) and heat at 80 to 90 C till clear. Cool to 40 to 50 C and add all other ingredients and mix. Cool to room temperature. An off-white gel-like product is obtained.

Example 10

Sunburn Prevention Gel

Ingredients. (1) C12-15 Alkyl Benzoate 92.00 (2) Dibutyl Lauroyl Glutamide 1.0 (3) EUK-134 0.1 (4) Triethyl citrate 5.0 (5) Magnolol (and Honokiol 0.2 (6) Manganese Urocanate Glycinate 0.5 (7) Tetrahydrocurcuminoids 0.2 (8) Silybin 1.0. Procedure. Mix (1) and (2) and heat at 95 to 110 C till clear. Cool to 40 to 50 C and add all other ingredients and mix. Cool to room temperature. A translucent gel-like product is obtained.

Example 11

Skin Peroxide Reduction Anti-Wrinkle Sunscreen Lotion

Ingredients. (1) Water 69.36 (2) Acrylates/C10-30 Alkyl Acrylate

Crosspolymer 0.5 (3) EUK-134 0.1 (4) Sodium Stearyl Phthalamate 1.0 (5) Sodium Hydroxide 0.14 (6) Cetyl Alcohol 4.0 (7) Phenoxyethanol 0.7 (8) Chlorphenesin 0.3 (9) Octyl methoxycinnamate 5.0 (10) Ethylhexylglycein 0.5 (11) Benzophenone-3 2.0 (12) PEG-6 10.0 (13) Tetrahydrocurcuminoids 0.1 (14) Magnolol 0.1 (15) Paeonol 0.2 (16) Galanga Extract 5.0 (17) Fragrance 1.0. Procedure. Mix (1) to (11) and heat at 80 to 90 C till clear. Cool to 45 to 55. Pre-mix (12) to (16) and add to main batch and mix. Cool to room temperature and adjust pH to 7.5.

Example 12

Sunburn Treatment Lotion

Ingredients. (1) Water 67.86 (2) Acrylates/C10-30 Alkyl Acrylate Crosspolymer 0.5 (3) Carnosine 0.1 (4) Sodium Stearyl Phthalamate 1.0 (5) Sodium Hydroxide 0.14 (6) Cetyl Alcohol 4.0 (7) Phenoxyethanol 0.7 (8) Sesamin 0.3 (9) Octyl methoxycinnamate 10.0 (10) Silybin 1.0 (11) Ethylhexylglycerin 0.5 (12) Polysorbate-20 2.0 (13) PEG-6 10.0 (14) Tetrahydrocurcuminoids 0.1 (15) EUK-134 0.1 (16) Manganese Adenosine Triphosphate 0.2 (17) Paeonol 0.5 (18) Fragrance 1.0. Procedure. Mix (1) to (17) and heat at 80 to 90 C till clear. Cool to 35 to 45. Add (18) and mix. Cool to room temperature and adjust pH to 7.5. A lotion is obtained.

Example 13

Sun-Block Gel with Heterocyclic Base Complex of Manganese

Ingredients. (1) Deionized water 20.0 (2) Zinc Zeolite 5.0 (3) Methylpropanediol 67.5 (4) Dimethicone copolyol 4.0 (5) Preservatives 0.5 (6) Manganese Urocanate 1.0 (7) Ammonium Acryloyldimethyltaurate/VP copolymer 2.0. Procedure. Make main batch by mixing (2) to (6) at room temperature. Pre-mix (1) and (7) to a clear paste and add to main batch with mixing. The product has an off-white gel-like appearance.

Example 14

Sunscreen Fluid Composition

Ingredients. (1) PEG-6 85.4 (2) Vitamin A Palmitate 0.1 (3) Vitamin E Acetate 0.1 (4) Phenoxyethanol 0.5 (5) Propyl Paraben 0.3 (6) Shea butter 1.0 (7) Apricot Kernel Oil 0.5 (8) Grapeseed Oil 0.5 (9) Kiwi Fruit Seed Oil 0.5 (10) Mango butter 0.5 (11) Hydroxypropyl Cellulose 0.5 (12) Zinc Zeolite 10.0 (13) Manganese Urocanate Glycinate 0.5 (14) Darutoside 0.5 (15) Vitamin K 0.1. Procedure. Mix all ingredients to a paste.

Example 15

UV Absorbing Peroxide Decomposing Butter Composition

Ingredients. (1) Grapeseed Oil 15.8 (2) Mango Butter 18.5 (3) Cocoa Butter 0.5 (4) Beeswax 1.0 (5) Aloe butter 0.2 (6) Avocado Butter 0.5 (7) Shea Butter 0.5 (8) Vitamin E 0.1 (9) Grapeseed Oil 2.0 (10) Dimethicone 1.0 (11) Hydrogenated Soybean Oil 35.0 (12) Sesame Oil 0.9 (13) Tinoguard TT 0.2 (14) Phenoxyethanol 0.5 (15) Propyl Paraben 0.2 (16) Zinc Zeolite 15.0 (17) Titanium Zeolite 2.0 (18) Esculoside 0.5 (19) Manganese Urocanate Acetate 0.5 (20) Vitamin K 0.1 (21) Corn starch 5.0. Procedure: Mix all ingredients and heat at 60 to 70 C. Cool to room temperature. A butter-like material is obtained.

Example 16

Sunscreen Emollient Paste

Ingredients. (1) Paraffin Wax 25.0 (2) Propyl Paraben 0.1 (3) Cetyl Alcohol 1.0 (4) GMS-SE 4.0 (5) Stearic Acid 3.0 (6) Polawax 5.0 (7) Deionized Water 44.0 (8) Methyl Paraben 0.2 (9) Aloe vera 0.2 (10) Triethanolamine 0.5 (11) Dimethicone/Dimethiconol 2.0 (12) Zinc Zeolite 10.0 (13) Titanium Zeolite 4.0 (14) Manganese Urocanate 0.5 (15) EUK-134 0.5. Procedure. Mix ingredients (1) to (11) and heat at 80 to 90 C to a uniform mixture. Cool to 40 to 50 C. Add all other ingredients and mix. Cool to room temperature. An off-white paste is obtained.

Example 17

Sunscreen Powder

Ingredients. (1) Corn Starch 70.0 (2) Zinc Zeolite 14.0 (3) PEG-6 5.0 (4) Titanium Zeolite 5.0 (5) Tetrahydrocurcumin 0.5 (6) Manganese Urocanate Glycinate 0.5 (7) Dimethicone 5.0. Procedure. Mix (1) and (2). Premix (3) to (6) and add to main batch and mix. A powder composition is obtained.

Example 18

The Three-Step Topical Treatment Method

The three-step topical treatment method of the present invention comprises; (i) the mixing of a heterocyclic complex of manganese, wherein manganese is covalently bound to at least two oxygen atoms and coordinately bound to at least two nitrogen atoms and having general chemical structure according to FIG. 1, and (ii) a sunscreen agent, and (iii) topical application of said mixture, and wherein (iv) said treatment method is for the reduction of topical peroxide including hydrogen peroxide. To illustrate this in practical terms, a composition is prepared according to Example 1. It is mixed with a sunscreen agent in a desirable quantity. The mixture is applied to an area of skin where decomposition of topical peroxide is desired.

Example 19

The Three-Step Topical Treatment Method Using a Sunscreen Cream Base

The three-step topical treatment method of the present invention comprises; (i) the mixing of a heterocyclic complex of manganese, wherein manganese is covalently bound to at least two oxygen atoms and coordinately bound to at least two nitrogen atoms and having general chemical structure according to FIG. 1, and (ii) a sunscreen agent, and (iii) a carrier base, and (iv) topical application of said mixture, and wherein (v) said treatment method is for the reduction of sunburn and hydrogen peroxide. To illustrate this in practical terms, a composition is prepared according to Example 8. The mixture is applied to an area of skin where decomposition of topical peroxide is desired.

The invention claimed is:

1. A heterocyclic complex comprising manganese, wherein said manganese is covalently bound to at least two oxygen atoms and, wherein, said base having at least one nitrogen atom in its ring structure coordinately bound to said manganese; wherein said complex is selected from the group consisting of manganese cis-urocanate, (I);

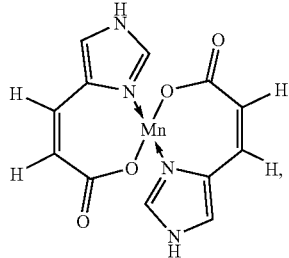

manganese cis-urocanate gluconate, (II);

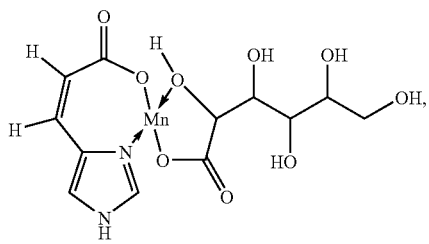

manganese cis-urocanate glycinate, (III),

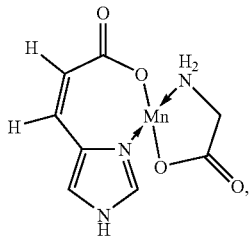

and combinations thereof.

2. A composition comprising at least one complex of claim 1.

3. A composition comprising at least one complex of claim 1 for the treatment of a skin condition selected from the group consisting of topical inflammation, damage from topical peroxide, and damage from UVA, UVB, and UVC radiation.

4. A composition comprising at least one complex of claim 1 and a sunscreen agent.

5. A composition comprising at least one complex of claim 1 further comprising a second heterocyclic complex selected from the group consisting of manganese adenosine triphosphate, manganese adenosine diphosphate, manganese adenosine mono-phosphate, manganese adenosine triphosphate glycinate, manganese adenosine triphosphate amino acetate, manganese adenosine diphosphate amino acetate, manganese adenosine mono-phosphate amino acetate, manganese benfotiamine glycinate, manganese benfotiamine, manganese benfotiamine amino acetate, manganese benfotiamine gluconate, ((N,N'-bis(3-methoxysalcylidene)ethylenediamine))Manganese Chloride: EUK-134, and combinations thereof.

6. The complex of claim 1, wherein said heterocyclic complex is manganese cis-urocanate of formula (I);

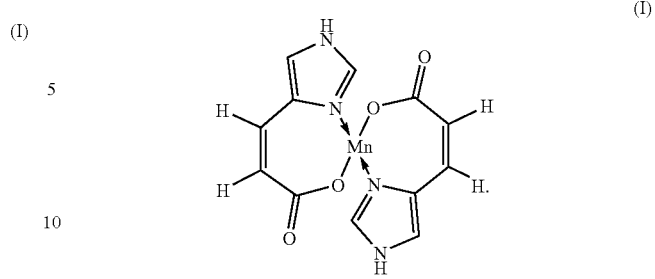

7. A composition comprising at least one complex of claim 1 further comprising a sunscreen agent selected from the group consisting of zinc oxide, galanga extract, titanium dioxide, para-aminobenzoic acid, avobenzone, 3-benzylidene camphor, benzylidene camphor sulfonic acid, bisymydazilate, camphor benzalkonium methosulfate, polyquaternium-59, cinnamidipropyltrimonium chloride, diethylamino hydroxybenzoyl hexyl benzoate, diethylhexyl butamido triazone, dimethicodiethylbenzal malonate, drometrizole trisiloxane, ecamsule, ensulizole, homosalate, isoamyl p-methoxycinnamate, 4-methylbenzylidene camphor, octocrylene, octyl dimethyl para-aminobenzoate, cinoxate, dioxybenzone, octyl methoxycinnamate, octyl salicylate, octyl triazone, oxybenzone, PEG-25 para-aminobenzoate, polyacrylamidomethyl benzylidene camphor, sulisobenzone, methyl anthranilate, trolamine salicylate, benzophenone-3, benzophenone-4, bisoctrizole, bemotrizinol, zinc zeolite, titanium zeolite, and combinations thereof.

8. A composition according to claim 7, wherein said sunscreen agent is benzophenone-3.

9. A composition comprising at least one complex of claim 1 further comprising a delivery system selected from the group consisting of a water and oil emulsion, a suspension, a colloid, a micro emulsion, a solution, a suspension of nanoparticles, an emulsion of nanoparticles, and an anhydrous composition.

10. A method of treating a skin condition comprising the topical application of a composition comprising at least one complex of claim 1 on an afflicted area, and wherein said application is repeated as desired.

11. The method of claim 10, wherein said skin condition is selected from the group consisting of damage from peroxides; skin wrinkles; and damage from UVA, UVB, and UVC radiation.

12. The composition of claim 5, wherein said second heterocyclic complex is manganese benfotiamine gluconate.

13. The method of claim 11, wherein said skin condition is skin wrinkles.

14. The complex of claim 1, wherein said heterocyclic complex is manganese cis-urocanate gluconate of formula (II);

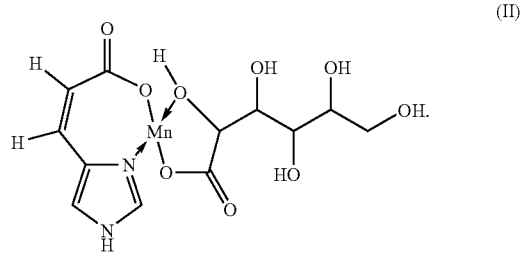

15. The complex of claim 1, wherein said heterocyclic complex is manganese cis-urocanate glycinate of formula (III);

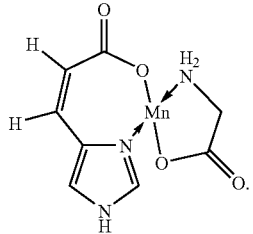
(III)

16. A composition according to claim 5, wherein said second heterocyclic complex is manganese adenosine triphosphate.

17. The composition of claim 5, wherein said second heterocyclic complex is ((N,N'-bis(3-methoxysalicylidene)ethylenediamine))Manganese Chloride EUK-134.

18. The composition of claim 3, wherein said treatment is for damage from UVA, UVB, and UVC radiation.

19. The composition of claim 9, wherein said delivery system is selected from the group consisting of a water and oil emulsion, a suspension, a colloid, a micro emulsion, a solution, a suspension of nanoparticles, an emulsion of nanoparticles, and an anhydrous composition.

20. The composition of claim 19, wherein said delivery system is a water and oil emulsion.

* * * * *